US006967020B2

(12) United States Patent
Tsuchida et al.

(10) Patent No.: US 6,967,020 B2
(45) Date of Patent: Nov. 22, 2005

(54) OXYGEN CARRIER SYSTEM, ARTIFICIAL OXYGEN CARRIER, AND REDUCING AGENT

(75) Inventors: Eishun Tsuchida, Tokyo (JP); Shinji Takeoka, Tokyo (JP); Yuji Teramura, Tokyo (JP); Tomoyasu Atoji, Tokyo (JP)

(73) Assignee: Oxygenix Co., Ltd, Tokyo (JP)

( * ) Notice: Subject to any disclaimer, the term of this patent is extended or adjusted under 35 U.S.C. 154(b) by 0 days.

(21) Appl. No.: 10/927,047

(22) Filed: Aug. 27, 2004

(65) Prior Publication Data

US 2005/0025757 A1    Feb. 3, 2005

Related U.S. Application Data

(63) Continuation of application No. PCT/JP03/02234, filed on Feb. 27, 2003.

(30) Foreign Application Priority Data

Feb. 27, 2002   (JP)   .............................. 2002-051732

(51) Int. Cl.$^7$ ........................ A61K 38/44; A61K 9/127
(52) U.S. Cl. .................... 424/94.4; 424/450; 424/455; 514/6
(58) Field of Search .............................. 424/450–455, 424/94.4; 514/6

(56) References Cited

U.S. PATENT DOCUMENTS

2002/0095108 A1 *  7/2002  Tsuchida et al. ............ 604/6.08

FOREIGN PATENT DOCUMENTS

JP       04-059735 A       2/1992
WO      WO 01/95930 A1    12/2001

OTHER PUBLICATIONS

Takeoka, S., et al. 1997 Methemoglobin Formation in Hemoglobin Vesicles and Reduction by Encapsulated Thiols. Bioconjugate Chem. 8: 539-544.*

Ljubomir Djordjevich, et al., "Lipid Encapsulated Hemoglobin as a Synthetic Erythrocyte", Federation Proceedings, vol. 36, No. 3, 1977, p. 567.

S. Takeoka, et al., "Evaluation of the Oxygen Transporting Capability of Hemoglobin Vesicles", Blood Substitutes, Present and Future Perspectives, 1998, pp. 171-184.

Hiromi Sakai, et al., "Suppression of Methemoglobin Formation by Glutathione in a Concentrated Hemoglobin Solution and in a Hemoglobin-Vesicle", Bull. Chem. Soc. Jpn., vol. 67, No. 4, 1994, pp. 1120-1125.

Shinji Takeoka, et al., "Methemoglobin Formation in Hemoglobin Vesicles and Reduction by Encapsulated Thiols", Bioconjugate Chem., vol. 8, No. 4, 1997, pp. 539-544.

Hiromi Sakai, et al., "Photoreduction of Methemoglobin by Irradiation in the Near-Ultraviolet Region", Biochemistry, vol. 39, No. 47, 2000, pp. 14595-14602.

Hiromi Sakai, et al., "Physical Properties of Hemoglobin Vesicles as Red Cell Substitutes", Biotechnol. Prog., vol. 12, No. 1, 1996, pp. 119-125.

Hiromi Sakai, et al., "Surface Modification of Hemoglobin Vesicles with Poly(ethylene glycol) and Effects on Aggregation, Viscosity, and Blood Flow during 90% Exchange Transfusion in Anesthetized Rats", Bioconjugate Chem., vol. 8, No. 1, 1997, pp. 23-30.

Teraoka et al, Polymer Preprints, Japan, vol. 51, No. 5, 2002, p. 956.

Takeoka et al, Bull. Chem. Soc. Jpn., vol. 70, 1997, pp. 1171-1178.

* cited by examiner

Primary Examiner—Karen Cochrane Carlson
Assistant Examiner—Marsha Tsay
(74) Attorney, Agent, or Firm—Oblon, Spivak, McClelland, Maier & Neustadt, P.C.

(57) ABSTRACT

An oxygen carrier system includes an artificial oxygen carrier including hemoglobin vesicles encapsulating hemoglobin and an intermediate electron mediator having a standard electrode potential of 0.05 V to 0.56 V (vs. the standard hydrogen electrode) in the vesicles, and a reducing agent which is added to an external aqueous phase of the hemoglobin vesicle to reduce methemoglobin when the hemoglobin encapsulated in the hemoglobin vesicle is oxidized to the methemoglobin. The reducing agent has, as an active component, at least one compound selected from the group consisting of a thiol compound and a reducing sugar.

18 Claims, No Drawings

OXYGEN CARRIER SYSTEM, ARTIFICIAL OXYGEN CARRIER, AND REDUCING AGENT

CROSS-REFERENCE TO RELATED APPLICATIONS

This is a Continuation Application of PCT Application No. PCT/JP03/02234, filed Feb. 27, 2003, which was published under PCT Article 21(2) in Japanese.

This application is based upon and claims the benefit of priority from prior Japanese Patent Application No. 2002-051732, filed Feb. 27, 2002, the entire contents of which are incorporated herein by reference.

BACKGROUND OF THE INVENTION

1. Field of the Invention

The present invention relates to an oxygen carrier comprising hemoglobin vesicles, and more particularly, to an oxygen carrier system having a reducing agent capable of reducing methemoglobin to which hemoglobin has been oxidized.

2. Description of the Related Art

In a current blood transfusion system, there are pointed out problems that 1) there is a possibility of infection (hepatitis, AIDS virus etc.), 2) a storing time limit for erythrocyte is about 3 weeks, 3) with advent of an aging society, a ratio of aged person among blood transfused patients is increased, while a total of healthy blood donors continues to be decreased, 4) there is a risk of contamination during storage of erythrocyte, 5) blood transfusion can not be applied to a patient who rejects blood transfusion for the religious reasons, and 6) the system can not be applied to emergent demand at disaster.

Therefore, demand for blood cell substitutes which can instantly respond at any time anywhere regardless of a blood group is increasing. As one of substitutes, transfusion preparations such as an electrolyte transfusion and a colloidal transfusion have been widely used, but these transfusion preparations do not have a function of erythrocyte of carrying oxygen which is the most important function of blood. Therefore, exploitation of a transfusion having oxygen carrying ability (oxygen infusion) is urgently demanded.

Recently, exploitation of an oxygen infusion using hemoglobin obtained by purifying hemoglobin (e.g., human hemoglobin, bovine hemoglobin, recombinant hemoglobin) which binds to and dissociates oxygen in erythrocyte, and chemically modifying the purified hemoglobin, is being progressed. Intermolecular crosslinked (polymerized) hemoglobin, water-soluble polymer-bound hemoglobin, and intermolecular crosslinked polymerized hemoglobin have been subjected to a clinical trial in Europe and USA. However, regarding an oxygen infusion using these chemically modified hemoglobins, various side effects due to naked hemoglobin having no cell-type structure as erythrocyte have been pointed out. Accompanied with this, importance of a cell-type structure in which hemoglobin is encapsulated into a vesicle has been revealed.

Since it was found that phospholipid which is a biomembrane component alone forms a vesicle, and in Djordjevich et al., Fed. Proc. 36, 567, 1977, a system in which hemoglobin is encapsulated in a vesicle composed of phospholipid/cholesterol/fatty acid (hemoglobin vesicle) was studied, some groups including a group of the present inventors intensively studied a hemoglobin vesicle. A hemoglobin vesicle has advantages that 1) hemoglobin is not modified, 2) a viscosity, a colloidal osmotic pressure and an oxygen affinity can be adjusted to an arbitrary value, 3) a retention time in blood circulation is extended, and 4) various additives can be encapsulated into an aqueous phase in the vesicle at an arbitrary concentration. A group of the present inventors has previously established independently an effective process for preparing a hemoglobin vesicle, obtained a hemoglobin vesicle dispersion having various physical property values extremely near those of blood, and confirmed excellent oxygen carrying ability and safety thereof also in an animal experiment (Tsuchida ed., Blood Substitutes: Present and Future Perspective, Elsevier, Amsterdam, 1998).

Hemoglobin contains four hemes, and when the central iron is divalent ($Fe^{2+}$), hemoglobin can reversibly bind to oxygen, and becomes oxyhemoglobin under atmospheric air. On the other hand, methemoglobin in which a central iron becomes electron oxidation-type trivalent ($Fe^{3+}$) can not bind to oxygen. In addition, superoxide anion and hydrogen peroxide are produced accompanied with conversion of oxyhemoglobin to methemoglobin, and they act as an oxidizing agent to promote production of methemoglobin. There are methemoglobin reductase and active oxygen extinguishing enzyme in erythrocyte, and mechanism of maintaining a methemoglobin content at a level of 1% or lower is exerted. However, in an oxygen infusion using hemoglobin, since these enzymes are removed at purification of hemoglobin, hemoglobin is easily oxidized during storage and after administration, and oxidized hemoglobin (methemoglobin) is not reduced, thereby extinguishing oxygen carrying ability.

In order to reduce this methemoglobin, various methods have been proposed. For example, a method of encapsulating a reducing agent such as glutathione, homocysteine and ascorbic acid, or active oxygen extinguishing enzyme such as catalase and superoxide dismutase in a hemoglobin vesicle (Sakai et al., Bull. Chem. Soc. Jpn., 1994 and Takeoka et al., Bioconjugate Chem., 8, 539–544, 1997), a method of introducing methylene blue as an electron transporting substance into a vesicle membrane, and reducing hemoglobin in a vesicle by an electron transport mechanism from NADH added to an external aqueous phase of a vesicle (Takeoka et. al., Bull. Chem. Soc. Jpn., 70, 1171–1178, 1997), and a method of reducing methemoglobin by irradiation with the light in a near ultraviolet region (Sakai et al., Biochemistry, 39, 14595–14602, 2000) have been tried.

Among the aforementioned reducing methods, in a method of encapsulating a reducing agent such as glutathione and homocysteine together with purified hemoglobin into a vesicle, since a reducing agent is auto-oxidized and inactivated more rapidly than a rate of auto-oxidizing hemoglobin into methemoglobin, efficacy is low. In addition, a reducing agent produces active oxygen such as superoxide anion and hydrogen peroxide at the auto-oxidation, and this converts oxyhemoglobin to methemoglobin or ferrylhemoglobin.

Accordingly, an object of the present invention is to provide a system which uses a reducing agent, but further effectively reduces methemoglobin in a hemoglobin vesicle.

BRIEF SUMMARY OF THE INVENTION

The present inventors have systematically conducted fundamental studies concentrating on a hemoglobin vesicle and regarding electron transfer between hemoglobin or heme and a reducing agent, and substance transfer in a bilayer membrane over many years. As a result, the inventors have found that when an intermediate electron mediator is encapsulated in a hemoglobin vesicle, and hemoglobin in the vesicle is oxidized to methemoglobin, oxygen binding ability of hemoglobin is easily recovered by adding a reducing agent to an external aqueous phase of the vesicle, leading to the present invention.

Thus, according to the present invention, there is provided an oxygen carrier system comprising: an artificial oxygen carrier comprising hemoglobin vesicles encapsulating hemoglobin and an intermediate electron mediator having a standard electrode potential of 0.05 V to 0.56 V (vs. the standard hydrogen electrode) in the vesicles; and a reducing agent comprising, as an active component, at least one compound selected from the group consisting of a thiol compound and a reducing sugar, which is added to an external aqueous phase of the hemoglobin vesicle to reduce methemoglobin when the hemoglobin encapsulated in the hemoglobin vesicle is oxidized to the methemoglobin.

In addition, according to the present invention, there is provided an artificial oxygen carrier comprising hemoglobin vesicles encapsulating hemoglobin and an intermediate electron mediator having a standard electrode potential of 0.05 V to 0.56 V (vs. the standard hydrogen electrode) in the vesicles.

Further, according to the present invention, there is provided a reducing agent comprising, as an active component, at least one compound selected from the group consisting of a thiol compound and a reducing sugar, which is added, when in an oxygen carrier comprising hemoglobin vesicles encapsulating hemoglobin and an intermediate electron mediator having a standard electrode potential of 0.05 V to 0.56 V (vs. the standard hydrogen electrode) in the vesicles the hemoglobin is oxidized to methemoglobin, to the external aqueous phase of the hemoglobin vesicles to reduce the methemoglobin.

In the present invention, the hemoglobin vesicle is usually in the form in which the vesicle is dispersed in an aqueous medium.

The active component of the reducing agent can be selected from the group consisting of cysteine, homocysteine, N-acetylcysteine and thioglycolic acid, and the reducing agent can be in the form of an aqueous solution, or in the form of a powder or a tablet.

In the present invention, the intermediate electron mediator exhibits a standard electrode potential of preferably 0.07 to 0.55 V, and can be selected from the group consisting of a compound having a phenazine ring, a compound having a phenothiazine ring, a compound having a phenazonium ring, a compound having an isoalloxazine ring, and a compound having a nicotine amide group.

The hemoglobin vesicle can further encapsulate an extinguishing enzyme for active oxygen species.

DETAILED DESCRIPTION OF THE INVENTION

The present invention will be explained in detail below.

The oxygen carrier system of the present invention comprises an artificial oxygen carrier containing a given hemoglobin vesicle, and a reducing agent. The hemoglobin vesicle contains hemoglobin and an intermediate electron mediator therein.

Hemoglobin encapsulated in the vesicle exerts central function of an artificial oxygen carrier, and binds to or releases oxygen due to a difference in oxygen partial pressure. Hemoglobin can be obtained from erythrocyte derived from a living body, human erythrocyte derived from donation, or erythrocyte derived from livestock such as pig, sheep and cow. For example, according to the known procedure, an erythrocyte membrane (stroma) is removed from erythrocyte by a hypotonic hemolysis method, this is heated at 60° C. for 1 hour or longer to inactivate virus, and is purified. The thus obtained high purity stroma-free hemoglobin can be suitably used. By the heat treatment noted above, a methemoglobin reductase system present in erythrocyte is denatured, and is inactivated. Alternatively, recombinant hemoglobin derived from a recombinant gene of cells of *Escherichia coli* and yeast, or animal or plant cells is purified and concentrated, which can be used.

A component constituting a membrane structure of the vesicle is not limited as far as it is an amphiphilic molecule or a surfactant which forms a bilayer membrane and has high biocompatibility, but lipid, preferably, phospholipid is used. Phospholipids used in the present invention is not particularly limited, but glycerophospholipid such as phosphatidylcholine, phosphatidylethanolamine, phosphatidylserine, phosphatidylinositol, phosphatidylglycerol, and diphosphatidylglycerol, and sphingophospholipid such as sphingomyelin can be used. A mixture of these phospholipids may be used. It is preferable to add cholesterol to a vesicle membrane.

The intermediate electron mediator used in the present invention is encapsulated as an oxidized form in the hemoglobin vesicle. When a reducing agent described in detail below is added to an external aqueous phase of the hemoglobin vesicle, and is permeated through the vesicle membrane into the vesicle, the intermediate electron mediator is reduced with the reducing agent into a reduced form, and this reduced entity reduces rapidly methemoglobin in the hemoglobin vesicle. This intermediate electron mediator exhibits a standard electrode potential of 0.05 V to 0.56 V, preferably 0.07 to 0.55 V (vs. the standard hydrogen electrode), and can be stably introduced in the vesicle, and any compound can be used, as far as it is a compound having high biocompatibility. Preferable examples of the compound include a compound having a phenazine ring such as phenazine methosulfate, a compound having a phenothinozine ring such as methylene blue, a compound having a phenazonium ring such as cresyl blue, a compound having an isoalloxanzine ring such as flavins (e.g. flavin mononucleotide (FMN), flavin adenine dinucleotide (FAD), lumiflavin, dichlororiboflavin, riboflavin (vitamin $B_{12}$), and 10-methylisoalloxazine), and a compound having a nicotine amide group such as NADH and NADPH. These compounds can be used alone, or in combination of them.

In the present invention, the hemoglobin vesicle can be prepared utilizing the known procedure (Sakai et al., Biotechnol. Progress, 12, 119–125, 1996; Bioconjugate Chem. 8, 23–30, 1997). That is, the hemoglobin vesicle can be prepared by inclusion of an intermediate electron mediator in an aqueous concentrated hemoglobin solution to be contained in a vesicle, in preparing the hemoglobin vesicle by the known method. The hemoglobin vesicle is obtained in the form in which the vesicle is dispersed in an aqueous medium such as physiological saline. That is, it is preferable that the concentrated dispersion of the hemoglobin vesicle obtained by the aforementioned method is diluted with physiological saline or the like. It is preferable that this diluted hemoglobin vesicle dispersion has the hemoglobin concentration in the dispersion of 5 to 15 g/dL. By this dilution, the concentrations of the hemoglobin and intermediate electron mediator in the hemoglobin vesicle are not substantially diluted. Alternatively, an outer surface of the hemoglobin vesicle may be modified with polyethylene glycol. This modification can be performed, for example, by adding polyethylene glycol-bound phospholipid to the resulting hemoglobin vesicle dispersion.

It is preferable that the hemoglobin concentration in the hemoglobin vesicle constituting the artificial oxygen carrier of the invention is 30 to 45 g/dL. Further, it is preferable that the concentration of the intermediate electron mediator in this hemoglobin vesicle is 10 to 20 $\mu$M.

The reducing agent used in the present invention can permeate through the hemoglobin vesicle membrane and reach an inner aqueous phase of the vesicle. The reducing agent also has biocompatibility, and is water-soluble. Such a reducing agent contains, as an active component, at least one compound selected from the group consisting of a thiol compound and a reducing sugar. Examples of the thiol compound used as an active component of the reducing agent include cysteine, homocysteine, N-acetylcysteine and thioglycolic acid. In addition, examples of the reducing sugar used as an active component of the reducing agent include ribose and glucose. These compounds can be used alone, or in combination of them. These thiol compound and reducing sugar are compounds which can be administered to a living body by intravenous or oral administration, and are currently blended in a medicine. As the active component of the reducing agent, a thiol compound is preferable, and cysteine is particularly preferable. The reducing agent of the invention can be used in the form of an aqueous solution (e.g. solution in physiological saline), a powder or a tablet.

In the oxygen carrier system of the invention, when hemoglobin in a hemoglobin vesicle in an artificial oxygen carrier is oxidized to methemoglobin, a reducing agent is added to an external aqueous phase of the hemoglobin vesicle. The reducing agent added to the external aqueous phase of the hemoglobin vesicle permeates through a hemoglobin vesicle membrane, enters an inner aqueous phase of the vesicle, and reduces an oxidized form of intermediate electron mediator of the hemoglobin vesicle to convert the medium to a reduced form. The reduction-type intermediate electron mediator reduces methemoglobin in the hemoglobin vesicle to hemoglobin, whereby, the oxygen binding ability of hemoglobin is recovered. Since a reaction of reducing methemoglobin with a reducing agent is a competitive reaction with oxygen oxidation of the reducing agent, that is, auto-oxidation of the reducing agent, the reducing agent first reduces an oxidized form of intermediate electron mediator into a reduced form, and this reduces methemoglobin, thereby, methemoglobin can be more rapidly reduced than auto-oxidation of the reducing agent. Since an intermediate electron mediator is present as an inert oxidized form when a reducing agent is not added, oxygen oxidation due to this does not occur, and therefore, conversion of hemoglobin to methemoglobin due to the oxidation does not progress.

Meanwhile, active oxygen species can be present in the hemoglobin vesicle. Such an active oxygen species is mainly hydrogen peroxide, and this can be produced by auto-oxidation of a reducing agent added from the outside of the hemoglobin vesicle, or auto-oxidation of a reduction-type intermediate electron mediator in the hemoglobin vesicle. More particularly, a superoxide anion is generated by the auto-oxidation, and this is converted into hydrogen peroxide by a dismutation reaction. Such an active oxygen species can shorten a life of the hemoglobin vesicle. Therefore, it is preferable that an extinguishing enzyme for active oxygen species is contained in the hemoglobin vesicle. As the active enzyme species extinguishing enzyme, catalase is particularly preferable. The active oxygen species extinguishing enzyme can be present at a mole ratio of 1/700 to 1/30 relative to a hemoglobin molecule in an inner phase of the hemoglobin vesicle.

The artificial oxygen carrier of the invention can be utilized as a blood cell substitute like erythrocyte, and can be used as a resuscitation solution upon hemorrhagic shock, or in extracorporeal circulation. An amount of methemoglobin in the hemoglobin vesicle can be measured by, for example, an ultraviolet and visible spectrometer. The reducing agent can be added by injecting into a vein by intravenous injection or drip, or can be added as an aqueous solution, a powder or a tablet by oral administration.

The reducing agent of the invention can be also applied to treatment of morbid state in which a part of a methemoglobin reduction system in erythrocyte in a living body is lacked congenitally, or a methemoglobin reduction system becomes not to function acutely by influence of a drug or the like, and a content of methemoglobin is increased. Since a substance corresponding to an intermediate electron mediator in the invention such as flavin, cytochrome cb5, NADH and NADPH is present in erythrocyte, by administering the reducing agent of the invention as explained above, the reducing agent permeates through an erythrocyte membrane, and can reduce methemoglobin. Erythrocyte is not artificial, but is an oxygen carrier.

Various aspects of the present invention have been explained above, but the invention is not limited to those aspects. In addition, it goes without saying that two or more of the aforementioned various aspects can be combined.

The following Examples illustrate the present invention, but the invention is not limited to them.

EXAMPLE 1

Under sterile atmosphere, an oxidized form of phenazine methosulfate was added to a high purity stroma-free hemoglobin solution (40 g/dL, 6.2 mM) obtained by purification of human erythrocyte derived from donation, to the concentration of 1 mM and 100 $\mu$m. Filtration with an FM microfilter (manufactured by Fuji Photo Film Co., Ltd.) having a pore diameter of 0.22 $\mu$m using Remolino (registered trade mark) (manufactured by Nippon Millipore) afforded a hemoglobin solution for charging. A mixed lipid powder, Presome PPG-I (mixture of phosphatidylcholine/cholesterol/phosphatidylglycerol; manufactured by Nippon Fine Chemical Co., Ltd.) was added in portions to the lipid concentration of 4.5% by weight, and this was stirred at 4° C. for 12 hours to obtain a hemoglobin-encapsulated multilayered vesicle. By an extrusion method using Remolino (registered trade mark), a particle diameter of a vesicle and the number of membrane layers were controlled. Thereupon, the FM microfilter was used in an order of a pore diameter of 3 $\mu$m, 0.8 $\mu$m, 0.65 $\mu$m, 0.45 $\mu$m, 0.3 $\mu$m, and 0.22 $\mu$m. The thus obtained hemoglobin vesicle dispersion was diluted with physiological saline and subjected to ultracentrifugation (50,000 g, 40 min), and the supernatant hemoglobin solution was removed by suction. To the resulting diluted vesicle dispersion was added polyoxyethylene-bound lipid (N-(monomethoxypolyethyleneglycol-carbamyl)distearoylphosphatidylethanolamide; molecular weight of polyethyleneglycol 5300) dispersed in physiological saline at an amount corresponding to 0.3 mol % of a lipid on an outer surface of the vesicle, and this was stirred at 25° C. for 2 hours to modify a surface of the hemoglobin vesicle with polyethylene glycol. The hemoglobin vesicle was precipitated by ultracentrifugation (50,000 g, 40 min), and re-dispersed in physiological saline so that the hemoglobin concentration became 10 g/dL. This was filtered with Dismic-25; 0.45 μm filter (ADVANTEC) to obtain a polyethylene glycol-modified hemoglobin vesicle dispersion. In addition, a high purity stroma-free hemoglobin solution (40 g/dL, 6.2 mM) with no phenazine methosulfate was subjected to the entirely same treatment, to obtain a polyethylene glycol-modified hemoglobin vesicle dispersion.

Sodium nitrite was added to the each resulting vesicle dispersion to oxidize almost 100% of hemoglobin in the vesicle. The vesicle was precipitated by ultracentrifugation, the supernatant sodium nitrite was completely removed, and the methemoglobin concentration was adjusted to 5.0 μM with a phosphate buffer (pH 6.4). It was shown from ultraviolet and visible absorption spectrum that, when under atmosphere, cysteine was added to the concentration of 50 mM, only 25% methemoglobin was reduced at 30 minutes in the hemoglobin vesicle with no phenazine methosulfate added, while 90% methemoglobin was reduced at 60 minutes in the phenazine methosulfate-encapsulated hemoglobin vesicle in all cases.

EXAMPLE 2

A flavin mononucleotide-encapsulated hemoglobin vesicle dispersion having the methemoglobin concentration of 5.0 μM was prepared in the same manner as that of Example 1 except that flavin mononucleotide was added to the concentration of 2 mM in place of phenazine methosulfate. When homocysteine was added to this dispersion to 30 mM under atmosphere, 60% of methemoglobin was reduced at 30 minutes.

EXAMPLE 3

A methylene blue-encapsulated hemoglobin vesicle dispersion having the methemoglobin concentration of 5.0 μM was prepared in the same manner as that of Example 1 except that methylene blue was added to the concentration of 6.5 mM in place of phenazine methosulfate. When ribose was added to this dispersion to the concentration of 60 mM under atmosphere, 50% of methemoglobin was reduced at 30 minutes.

EXAMPLE 4

A nicotineamide adenine dinucleotide/catalase-encapsulated hemoglobin vesicle dispersion having the methemoglobin concentration of 5.0 μM was prepared in the same manner as that of Example 1 except that nicotineamide adenine dinucleotide was added to the concentration of 2 mM, and catalase was added to the concentration of 10,000 units/mM in place of phenazine methosulfate. When cysteine was added to this dispersion to the concentration of 50 mM under atmosphere, 75% of methemoglobin was reduced at 30 minutes.

EXAMPLE 5

A Wister rat (male, weight 300 g) was intraperitoneally anesthetized with nenbutal, and a tube was inserted into carotid artery and jugular. The phenazine methosulfate-encapsulated hemoglobin vesicle (hemoglobin concentration 10 g/dL, 4 mL) prepared in Example 1 was administered through jugular at a rate of 1 mL/min. 1 mL of blood was taken out from carotid artery after 9 hours, this was placed into an EDTA-added blood collecting tube, and subjected to centrifugation (2000 g, 10 min) to obtain a hemoglobin vesicle dispersion as the supernatant. After it was confirmed by ultraviolet/visible absorption spectrum that 20% of hemoglobin was oxidized, 1 mL of blood was extracted from carotid artery 30 minutes after administration 1 mL of cysteine having the concentration of 60 mM through carotid artery. In the same manner, the methemoglobin concentration was measured, and was found to be 5%.

EXAMPLE 6

A Wister rat (male, weight 300 g) was intraperitoneally anesthetized with nenbutal, and a tube was inserted into carotid artery and jugular. 8 mL of blood was extracted from carotid artery, this was placed into an EDTA-added blood collecting tube, subjected to centrifugation (2000 g, 10 minutes), and washed with physiological saline three times to obtain washed erythrocyte. This erythrocyte was washed again with physiological saline three times after oxidation of hemoglobin with sodium nitrite, thereby, erythrocyte in which 20% of hemoglobin was oxidized was prepared, and this was administered through carotid artery. After 5 minutes, a cysteine tablet (1 tablet, cysteine 300 mg/tablet) was orally administered, 1 mL of blood was extracted from carotid artery after 30 minutes, and the methemoglobin concentration was measured according to the same procedure, and was found to be 2%.

EXAMPLE 7

A Wister rat (male, weight 300 g) was intraperitoneally anesthetized with nenbutal, and a tube was inserted into carotid artery and jugular. A phenazine methosulfate and catalase-encapsulated hemoglobin vesicle was prepared based on Example 1 (hemoglobin concentration 10 g/dL, catalase concentration $5.6 \times 10^4$ units/mL, 4 mL). This sample was administered through jugular at a rate of 1 mL/min. After 9 hours, 1 mL of blood was extracted through carotid artery, this was placed into an EDTA-added blood collecting tube, and subjected to centrifugation (2000 g, 10 min) to obtain a hemoglobin vesicle dispersion as the supernatant. After it was confirmed by ultraviolet/visible absorption spectrum that 15% of hemoglobin was oxidized to methemoglobin, 1 mL of blood was extracted through carotid artery 30 minutes after administration of 1 mL of cysteine having the concentration of 30 mM through carotid artery, and the methemoglobin concentration was measured in the same manner, and found to be 5%.

As described above, according to the present invention, there is provided a system for further effectively reducing methemoglobin in a hemoglobin vesicle by using a reducing agent.

What is claimed is:
1. An oxygen carrier system comprising:
    an artificial oxygen carrier comprising hemoglobin vesicles encapsulating hemoglobin and an intermediate electron mediator having a standard electrode potential of 0.05 V to 0.56 V (vs. the standard hydrogen electrode) in the vesicles; and
    a reducing agent which is at least one thiol compound or at least one reducing sugar, or both,
    wherein said reducing agent is added to an external aqueous phase of the hemoglobin vesicle to reduce methemoglobin when the hemoglobin encapsulated in the hemoglobin vesicle is oxidized to the methemoglobin.

2. The oxygen carrier system according to claim 1, wherein the hemoglobin vesicle further encapsulates an extinguishing enzyme for active oxygen species.

3. The oxygen carrier system according to claim 2, wherein the extinguishing enzyme for active oxygen species is a catalase.

4. The oxygen carrier system according to claim 1, wherein the hemoglobin vesicle is in a form in which the vesicle is dispersed in an aqueous medium.

5. The oxygen carrier system according to claim 1, wherein the reducing agent is a thiol compound selected from the group consisting of cysteine, homocysteine, N-acetylcysteine and thioglycolic acid.

6. The oxygen carrier system according to claim 1, wherein the reducing agent is in a form of an aqueous solution.

7. The oxygen carrier system according to claim 1, wherein the reducing agent is provided into the external aqueous phase in a form of a powder or a tablet.

8. The oxygen carrier system according to claim 1, wherein the intermediate electron mediator exhibits a standard electrode potential of 0.07 to 0.55 V (vs. the standard hydrogen electrode).

9. The oxygen carrier system according to claim 8, wherein the intermediate electron mediator is selected from the group consisting of a compound having a phenazine ring, a compound having a phenothiazine ring, a compound having a phenazonium ring, a compound having an isoalloxazine ring, and a compound having a nicotine amide group.

10. An artificial oxygen carrier comprising:
hemoglobin vesicles encapsulating hemoglobin and an intermediate electron mediator having a standard electrode potential of 0.05 V to 0.56 V (vs. the standard hydrogen electrode) in the vesicles,
wherein the electron mediator is reduced by a reducing agent comprising, as an active component, at least one compound selected from the group consisting of a thiol compound and a reducing sugar, which is added to the external aqueous phase of the hemoglobin vesicles and permeates through the hemoglobin vesicle membranes, wherein the reduced intermediate electron mediator reduces the methemoglobin formed within the vesicles.

11. The artificial oxygen carrier according to claim 10, wherein the hemoglobin vesicle further encapsulates an extinguishing enzyme for active oxygen species.

12. The artificial oxygen carrier according to claim 10, wherein the hemoglobin vesicle is in a form in which the vesicle is dispersed in an aqueous medium.

13. The artificial oxygen carrier according to claim 10, wherein the intermediate electron mediator exhibits a standard electrode potential of 0.07 to 0.55 V (vs. the standard hydrogen electrode).

14. The artificial oxygen carrier according to claim 13, wherein the intermediate electron mediator is selected from the group consisting of a compound having a phenazine ring, a compound having a phenothiazine ring, a compound having a phenazonium ring, a compound having an isoalloxazine ring, and a compound having a nicotine amide group.

15. A hemoglobin vesicle comprising:
encapsulated hemoglobin and an intermediate electron mediator having a standard electrode potential of 0.05 V to 0.56 V (vs. the standard hydrogen electrode),
and a reducing agent selected from the group consisting of at least one thiol compound or at least one reducing sugar, which has been added to an external aqueous phase and has permeated through the membranes of the hemoglobin vesicles and reduced methemoglobin in said vesicles.

16. The hemoglobin vesicle according to claim 15, wherein the active component is selected from the group consisting of cysteine, homocysteine, N-acetylcysteine and thioglycolic acid.

17. The hemoglobin vesicle according to claim 15, which has been produced by administering the reducing agent in a form of an aqueous solution.

18. The hemoglobin vesicle according to claim 15, which has been produced by orally administering a powder or tablet containing the reducing agent.

* * * * *